United States Patent [19]
Brownell et al.

[11] Patent Number: 5,654,997
[45] Date of Patent: Aug. 5, 1997

[54] ULTRASONIC RANGING SYSTEM FOR RADIATION IMAGER POSITION CONTROL

[75] Inventors: Thomas Arthur Brownell, Ballston Lake; Vivek Venugopal Badami, Niskayuna; John Lewis Schneiter, Latham; George Charles Goodman, Niskayuna, all of N.Y.

[73] Assignee: General Electric Company, Schenectady, N.Y.

[21] Appl. No.: 537,576

[22] Filed: Oct. 2, 1995

[51] Int. Cl.$^6$ .................................................. H05G 1/54
[52] U.S. Cl. ................................................ 378/117; 378/95
[58] Field of Search .......................... 378/117, 91, 204, 378/95; 340/540, 541; 367/93, 118, 124, 129

[56] References Cited

U.S. PATENT DOCUMENTS

| | | | |
|---|---|---|---|
| 4,320,766 | 3/1982 | Alihanka et al. | 128/671 |
| 5,019,804 | 5/1991 | Fraden | 340/562 |
| 5,097,495 | 3/1992 | Gray et al. | 378/91 X |
| 5,105,455 | 4/1992 | Kato et al. | 378/117 |
| 5,485,502 | 1/1996 | Hinton et al. | 378/117 |
| 5,486,700 | 1/1996 | Silberklang et al. | 250/363.04 |

OTHER PUBLICATIONS

Application entitled, "Imager Control System With Contact Detector," Serial No. 08/537,580, filed Oct. 2, 1995.
Application entitled, "Capacitive Proximity Detector for Radiation Imager Position Control," Serial No. 08/537,954, filed Oct. 2, 1995.

*Primary Examiner*—David P. Porta
*Attorney, Agent, or Firm*—Donald S. Ingraham

[57] ABSTRACT

An ultrasonic ranging system for providing a distance to a subject signal for use in positioning a movable imaging element support structure with respect to a subject of examination includes a collar assembly disposed around a portion of the imaging element structure disposed towards an imaging region; a plurality of ultrasonic transducers disposed in a sensing pattern around the collar assembly; and an ultrasonic ranging processing unit coupled to the transducers to control processing of ultrasonic ranging signals from the transducers. The transducers are typically disposed in one or more rows on the surface around the circumference of the collar assembly such that the lobes of ultrasonic signals generated provide a desired ranging field.

9 Claims, 2 Drawing Sheets

ULTRASONIC RANGING SYSTEM FOR RADIATION IMAGER POSITION CONTROL

BACKGROUND OF THE INVENTION

This invention relates generally to radiation imaging devices and in particular to proximity measuring systems for determining the position of components of the radiation imaging system with respect to a subject.

Medical radiation imagers, such as x-ray machines, must be accurately positioned close to the patient to provide the desired imaging information and such that components of the assembly do not physically collide with the patient. On some types of imaging equipment, such as computer tomography (CT) imagers or the like, a radiation detector, such as an x-ray image intensifier tube is positioned on a movable gantry arm opposite to another arm on which the x-ray source is disposed; the opposed arms can be swung around a part of a patient's body, such as the head. It is desirable that the radiation detector be positioned close to (e.g., within about 1 inch) but not touch any part of the patient as the gantry arm rotates. In such systems an operator commonly controls the position of the radiation detector by means of manual control, such as with a joystick arrangement. The end of the radiation detector assembly nearest the patient is surrounded by a donut-shaped air-bag assembly. In what is commonly called "Level I" sensing, if the air-bag assembly comes in contact with the patient, a detected change in air pressure in the air-bag causes the control system to direct cessation of movement of the system. A pressure difference of about 0.3" of water is commonly used as the threshold to prompt a Level I stop. A second level of sensing, Level II sensing, refers to a situation when an additional 0.1" change (beyond Level I) in air-bag pressure occurs, such as from slight over-travel in the gantry arm after reaching the Level I shutdown point. A Level II signal causes a complete motor shutdown and locking of the gantry arms; the Level II motor control is accomplished via hardwired relays outside of the normal computer-controlled gantry arm control circuits. After a Level II shutdown signal, the gantry arm assembly must be manually disengaged and hand-cranked away from the patient's body. This arrangement provides a dual-point failure mode in the sensing scheme. Most systems further have a contact switch disposed exterior to the air-bag that provides a further back up, such that physical contact resulting in activation of the contact micro-switches provides independent shutdown signals to the gantry arm control system.

Efficient and effective use of medical imaging equipment of this type is enhanced by operating modalities that follow the contour of the patient's body to maintain the radiation detector assembly at a desired separation from the nearest portion of the patient's body as the assembly is rotated around the body. It is desirable that no part of the radiation detector assembly and gantry arm come into contact with the patient's body at any time during the procedure, and further desirable that the control system be able to prevent contact with the patient and shutdown commands that are generated as a result of contact between the air-bag assembly disposed around the radiation detector and the patient.

SUMMARY OF THE INVENTION

An ultrasonic ranging system for providing a distance to a target signal for use in positioning a movable imaging element support structure with respect to the subject includes a collar assembly disposed around a portion of the imaging element structure disposed towards an imaging region; a plurality of ultrasonic transducers disposed in a sensing pattern around the collar assembly; and an ultrasonic ranging processing unit coupled to the transducers to control processing of ultrasonic ranging signals from the transducers. The transducers are typically disposed in one or more rows on the surface around the circumference of the collar assembly so that the lobes of the ultrasonic signals generated and detected by the transducers provide a desired ranging field with respect to the imaging element.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1:
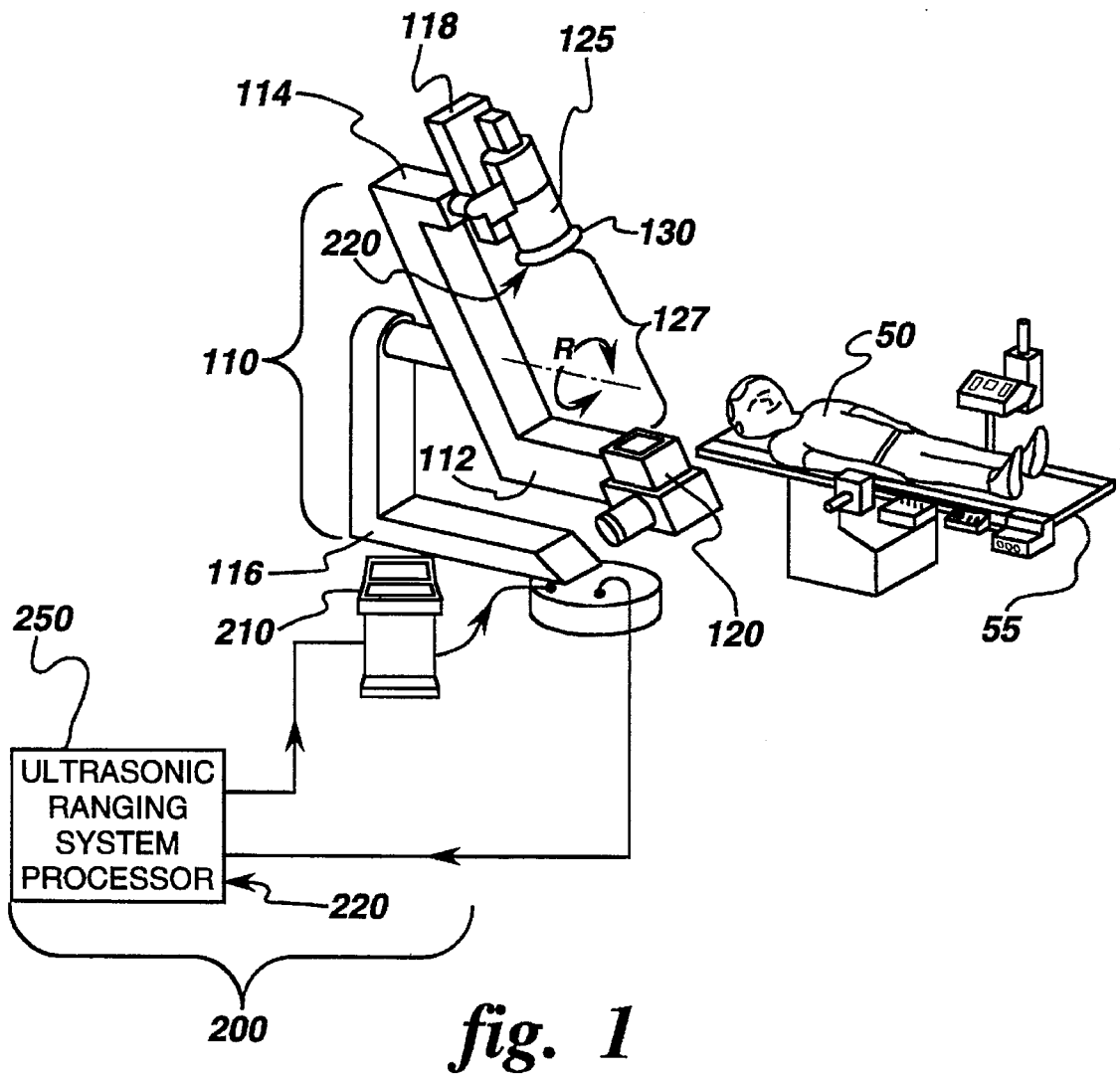
FIG. 1 is a part perspective and part block diagram of a radiation imaging system in accordance with this invention.

A radiation imaging system 100 comprises a movable gantry assembly 110 that is coupled to an imager control system 200 (FIG. 1). Control system 200 typically comprises an operator console 210 for commanding respective modalities of operation of imaging system 100, and an ultrasonic ranging system 220 having a processing unit 250. Control system 200 generates control signals corresponding to the proximity of components on gantry assembly 110 to the object being imaged so as to move gantry assembly 110 to a desired position with respect to the imaged object.

Gantry assembly 110 comprises a first arm 112 and a second arm 114 that provide a support structure for components of the radiation imaging system. Typically a radiation source 120 (such as an x-ray source or the like) is mounted on first arm 112 and radiation detector assembly 125, such as an x-ray image-intensifier tube (II-tube) or the like, is disposed on second arm 114 so as to be disposed opposite radiation source 120 across an intervening imaging region 127.

By way of example and not limitation, as presented herein radiation imaging system 100 is adapted for medical imaging of a patient's body; alternatively, the ultrasonic ranging system of this invention can be used with other types of radiation imaging, such as is used in industrial processes for quality control and the like. Typically the object of study, or a subject 50, is a portion of a patient's body, such as the patient's head, that is resting on an examining table 55. Gantry arms 112 and 114 are rotatably mounted on a gantry foundation 116 so that they can be rotated around subject 50, e.g., as indicated by the arrow "R" in FIG. 1. Radiation detector assembly 125 is further mounted on a movable slide 118 so that it can be disposed closer to or farther from radiation source 120, thus respectively decreasing or increasing the extent (or length between the source and detector components) of imaging region 127. Gantry assembly 110 and movable components thereon, such as slide 118, are typically driven by drive systems (not shown), such as an electrical motor and transmission, that are responsive to signals from control system 200.

When initially positioning the patient within imaging region 127, slide 118 is positioned to provide a large extent of imaging region 127; during the x-ray examination procedure, however, it is desirable that radiation detector assembly 125 be positioned in close proximity to subject 50, but not in physical contact with the subject. A collar assembly 130 is typically disposed around the end or portion of radiation detector assembly 125 that is closest to the surface of subject 50.

In accordance with this invention, ultrasonic ranging system 220 (FIG. 2) is coupled to radiation imaging system 100 so as to sense the position of radiation detector assembly 125 (FIG. 1) with respect to subject 50 and to generate signals to control the movement of gantry assembly 110 and components thereon (such as movable slide 118) so as to dispose radiation detector assembly 125 in a desired location with respect to subject 50. Typically ultrasonic ranging system 220 provides accurate and contemporaneous proximity sensing sensitivity so that signals can be generated by control console 210 to position movable slide 118 (and thus radiation detector assembly 125) automatically during an imaging process as gantry assembly 110 rotates around subject 50, thus reducing the time and inaccuracy associated with manual positioning of the gantry arm assembly with respect to subject 50 during an imaging process.

Figure 2A:
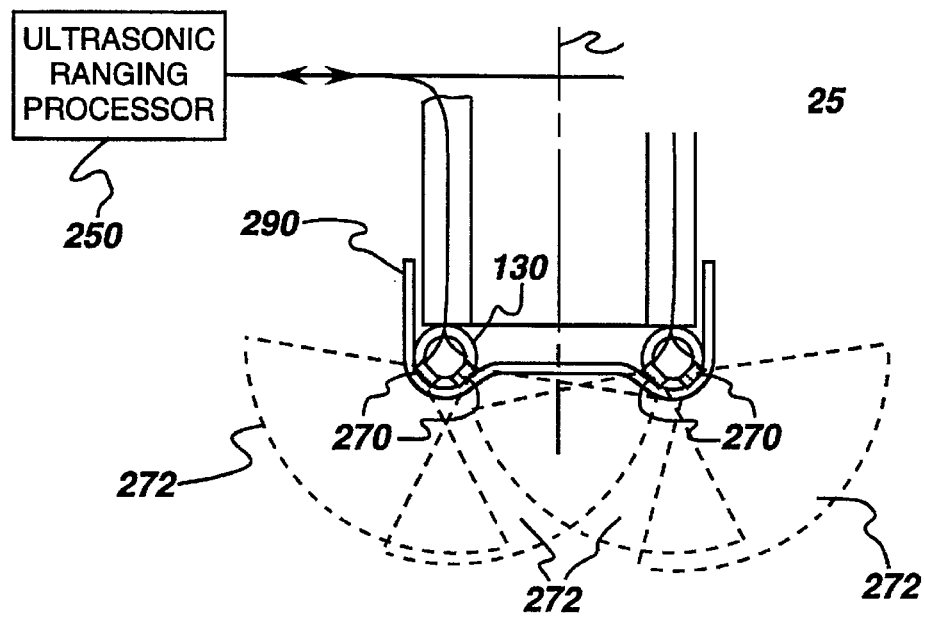
FIG. 2(A) is a cross-sectional view of a collar assembly having an ultrasonic ranging system in accordance with this invention.
Figure 2B:
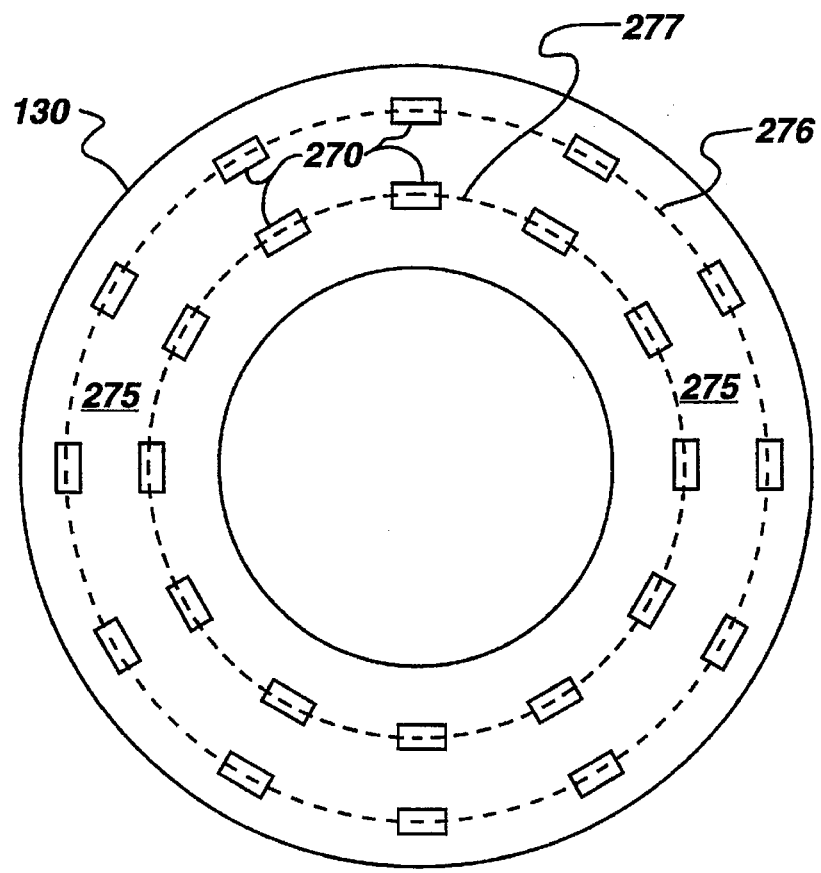
FIG. 2(B) is an end-view of a collar assembly having an ultrasonic ranging system in accordance with this invention.

In accordance with this invention, ultrasonic ranging system 220 comprises ultrasonic ranging processor 250 coupled to a plurality of ultrasonic transducers 270 disposed on collar assembly 130 in a sensing pattern 275 as illustrated in FIGS. 2(A) and 2(B). The sensing pattern is selected such that ultrasonic transducers 270 are disposed circumferentially around collar assembly 130, typically at equiangular intervals. Each ultrasonic transducer 270 comprises means for converting electrical signals into a corresponding acoustic signal and vice versa. Generally, the transducer comprises a housing having a piezo-electric element coupled to a backing material (not separately shown) such that an ultrasonic acoustic signal is generated in response to an electrical signal, and such that a received ultrasonic acoustic signal displaces the piezo-electric element so as to generate a corresponding electrical signal.

One example of ultrasonic transducers is the transducer manufactured by the Polaroid Corporation and sold as a "Polaroid Ultrasonic Ranging Unit". The Polaroid transducer includes a pliable conductive foil stretched over a grooved plate, forming the moving element that transforms electrical energy into sound waves and the returning echo into an electrical signal. The grooved, metallic backplate is in contact with the foil and forms a capacitor which, when charged, exerts an electrostatic force to the foil to cause the foil to move and generate the acoustic signal. By way of example and not limitation, such a commercially available transducer has the capability of detecting objects and distances (in an arrangment in accordance with this invention) between about one inch and in excess of two feet. Commonly multiple frequencies (that is, a plurality of respective ultrasonic frequencies) are transmitted by the transducer so as to avoid loss of signal resulting from high attenuation of a particular ultrasonic frequency by some feature of the subject that is being detected.

The total number of transducers disposed around collar assembly 130 in sensing pattern 275 are selected in the design process to provide a desired ranging distance and resolution of the subject. Ultrasonic transducers 270 are typically disposed in a row around the surface of collar assembly 130; sensing pattern 275 further may comprises one or more rows of transducers 270. Transducers 270 are positioned in rows such that a respective lobe 272 (FIG. 2(A)) of ultrasonic signals passing from the transducer covers a respective ranging field around collar assembly 130. The respective transducer lobes 272 (or ranging fields) that extend from respective transducers 270 collectively project over a region around collar assembly 130 in which the subject must be detected in order to properly position the gantry arm and radiation detector assembly 125.

By way of example and not limitation, a collar assembly 130 used in an x-ray imager application may have an outer diameter in the range of about 10 cm to about 40 cm, and may have a first transducer row 276 and a second transducer row 277; the transducers can be disposed in an aligned concentric arrangement as shown in FIG. 2, or in a staggered concentric arrangement such that a transducer in first row 276 is disposed at a position (in the line of first row transducers) between transducers in the second row. Additionally, transducers 270 are located on collar assembly to provide the desired subject detection capability; thus the beam shape, symmetry, and signal strength of a particular type of transducer must be taken into account in designing a particular sensing pattern 275 for the transducers. For example, in one embodiment, if the potential region in which the subject to be detected is relatively limited (e.g., within about 30° to 45° of a given radiation detector axis 127) with respect to the collar assembly, optimal detection and ranging information is developed when transducers 270 are positioned so that the center lobes of the beam overlap at the maximum desired detection distance. Alternatively, if the potential region in which the subject to be detected is greater than about 45° from a known axis 127, transducers 270 are commonly disposed on collar assembly 130 angled so that the respective lobes 272 overlap only somewhat (e.g., by about 45° or less) and thus provide collectively a larger ranging field (e.g., between about 90° and 210° around radiation detector axis 127) around collar assembly 130 (e.g., as illustrated in FIG. 2(A)). In either case, cost effectiveness dictates the use of as few transducers as necessary to accurately develop range data with respect to the subject being imaged.

By way of example and not limitation, commercially available transducers commonly have lobes 272 that are symmetric and have extent of about 120°, with a center lobe having an extent of 20° to 30° region around the center axis of the transducer. For a collar assembly having a diameter of about 10 cm., each row 276, 277 comprises between about 3 and 9 ultrasonic transducers, dependent upon the design resolution of the device. Typically transducers 270 are arranged in rows such that overlapping respective ranging fields 272 of transducers 270 cover a region of about 180° to about 270° around the portion of collar assembly that is disposed towards imaging region 127 (FIG. 1).

Processor 250 is coupled to each of the transducers 270 so as to control the generation of transmitted signals and processing of the received signals at the transducer. Processor 250 is adapted to provide respective transducer range signals from each of the transducers such that a signal corresponding to the position of the subject within the ranging fields (e.g., range information with respect to any of the transducer points around the surface of collar assembly 130 to localize the position of the subject with respect to the collar assembly) can be provided to control console 210 to control movement of gantry arm assembly 110.

A drape 290 is commonly disposed around collar assembly 130 to maintain sterile conditions around the patient. Drape 290 typically comprises a thin flexible sheet of polyethylene-type of material (e.g., having a thickness of less than about 0.005"). Drape 290 is attached to collar assembly 130 (with adhesive bands, fasteners, pneumatic means (such as drawing a partial vacuum across the drape, or the like) so as to be generally disposed in intimate contact with transducers 270 so as to provide adequate transmission of the ultrasound acoustic signals through drape 290 (typically attenuation is less than about 50%).

In operation, a patient is positioned on examining table 55 (FIG. 1) and imaging system 100 is commanded from control console 210 to commence the imaging process. Gantry arm 110 is positioned by the operator so as to dispose radiation detector assembly 125 in close proximity to the portion of the patient to be examined, e.g., the patient's head. Ultrasonic ranging system 220 is activated, and as the patient comes within the ranging fields of transducers 270, the ranging signals processed by processor 250 enable both the accurate determination of ranges to the patient and also the localization of contour features of the patient, such as ears, nose, etc. so that control console 210 can generate appropriate command signals to the gantry arm actuators (e.g., electrical motors or the like) so as to ensure that radiation detector assembly 125 is positioned at an optimal position with respect to the patient (without striking the patient) as gantry arm assembly 110 rotates around the patients head so that the imaging procedure can be completed.

It will be apparent to those skilled in the art that, while the invention has been illustrated and described herein in accordance with the patent statutes, modifications and changes may be made in the disclosed embodiments without departing from the true spirit and scope of the invention. It is, therefore, to be understood that the appended claims are intended to cover all such modifications and changes as fall within the true spirit of the invention.

What is claimed is:

1. An ultrasonic ranging system for providing a distance to a subject signal for use in positioning a movable imaging element support structure with respect to the subject, the ultrasonic ranging system comprising:
    a collar assembly disposed around at least a portion of said imaging element structure disposed towards an imaging region;
    a plurality of ultrasonic transducers disposed in a sensing pattern around said collar assembly; and
    an ultrasonic ranging processing unit coupled to said ultrasonic transducers so as to control ranging signals from said transducers and to generate range-to-subject signals, said ultrasonic ranging processing unit further being coupled to a gantry control device so as to provide said range-to-subject signals thereto for positioning said imaging element support structure with respect to said subject.

2. The ultrasonic ranging system of claim 1 wherein said collar assembly comprises a flexible tube having a circular shape, said ultrasonic transducers being mounted on the surface of said flexible tube disposed towards said imaging region.

3. The ranging system of claim 2 wherein the ultrasonic transducer sensing pattern comprises a row of transducers disposed at equiangular intervals around the circumference of said collar assembly.

4. The ranging system of claim 3 wherein said ultrasonic transducer sensing pattern further comprises more than one row of transducers disposed on the surface of said collar assembly, said transducers being disposed so as to project ultrasonic signal lobes along axes with respect to said movable imaging element structure so as to provide a ranging field in which said subject can be detected.

5. The ranging system of claim 1 wherein each of said ultrasonic transducers is adapted to generate and detect ultrasonic signals having a respective plurality of ultrasonic frequencies.

6. A radiation imaging system comprising:
    a gantry arm having a radiation imaging system component mounted thereon, said gantry being movably coupled to a positioning device so as to dispose said radiation imaging system component in a selectable spaced relationship with respect to a subject;
    a collar assembly disposed around said radiation imaging system component on said gantry arm;
    an ultrasonic ranging system coupled to said positioning device so as to control the position thereof, the ultrasonic ranging detection system comprising:
        a plurality of ultrasonic transducers disposed in a sensing pattern around said collar assembly; and
        an ultrasonic ranging processing unit coupled to said ultrasonic transducers so as to control transmission and receive processing of ranging signals from said transducers so as to generate a subject range signal.

7. The imaging system of claim 6 wherein said collar assembly has a ring-like shape and said ultrasonic transducers are disposed at equiangular intervals around the circumference of said collar assembly on a surface of said collar assembly oriented towards an imaging region.

8. The imaging system of claim 7 further comprising a patient protection drape disposed over said ultrasonic transducers and surface of said collar assembly oriented towards said imaging region, said shield being disposed on said collar assembly in contact with each of said transducers to provide acoustic coupling therethrough of said ranging signals.

9. The radiation imaging device of claim 6 wherein said radiation imaging system component comprises an x-ray image intensifier device.

\* \* \* \* \*